(12) United States Patent
Lane et al.

(10) Patent No.: US 6,242,201 B1
(45) Date of Patent: Jun. 5, 2001

(54) IDENTIFICATION OF THE P21$_{WAF1}$-PCNA INTERACTION SITE AND THERAPEUTIC APPLICATIONS THEREOF

(75) Inventors: David Philip Lane, Fife; Lynne Suzanne Cox, Oxford; Emma Warbrick, Fife; David Moore Glover, Perth, all of (GB)

(73) Assignee: Cyclacel Limited (GB)

( * ) Notice: Subject to any disclaimer, the term of this patent is extended or adjusted under 35 U.S.C. 154(b) by 0 days.

(21) Appl. No.: 08/817,895

(22) PCT Filed: Nov. 3, 1995

(86) PCT No.: PCT/GB95/02583

§ 371 Date: Aug. 22, 1997

§ 102(e) Date: Aug. 22, 1997

(87) PCT Pub. No.: WO96/14334

PCT Pub. Date: May 19, 1996

(30) Foreign Application Priority Data

Nov. 3, 1994 (GB) .................................................. 9422175

(51) Int. Cl.$^7$ ................................................. G01N 33/574
(52) U.S. Cl. ..................... 435/7.23; 530/326; 530/328; 514/2; 514/13; 514/16
(58) Field of Search .................................. 514/2, 13, 16; 435/7.23; 530/326, 328

(56) References Cited

U.S. PATENT DOCUMENTS

| | | | |
|---|---|---|---|
| 5,424,400 | 6/1995 | Smith | 530/350 |
| 5,596,079 | 1/1997 | Smith et al. | 530/328 |

FOREIGN PATENT DOCUMENTS

| | | |
|---|---|---|
| 2662698 | 12/1991 | (FR) . |
| 93/12251 | 6/1993 | (WO) . |
| WO 94/09135 | 4/1994 | (WO) . |
| 95/06415 | 3/1995 | (WO) . |
| 95/13375 | 5/1995 | (WO) . |
| 95/31995 | 11/1995 | (WO) . |
| 97/03681 | 2/1997 | (WO) . |

OTHER PUBLICATIONS

Hiraoka, Lea R., et al., "Sequence of Human FEN–1, a Structure–Specific Endonuclease, and Chromosomal Localization of the Gene (FEN1) in Mouse and Human" Genomics, (1995) vol. 25, pp. 220–225.

Xiong, Y., et al. "P21 is a universal inhibitor of cyclin kinases", Nature, vol. 366, (Dec. 16, 1993), pp. 701–704.

Harper, J., et al. "The p21 Cdk–Interacting Protein Cip1 is a Potent Inhibitor of G1 Cyclin–Dependent Kinase", Cell, vol. 75 No 4, (Nov. 19, 1993), pp. 805–816.

Chemical Abstracts, Abstract No. 233798u, vol. 122 No. 19, (May 8, 1995), Columbus, Ohio.

Warbrick, E., et al. "A small peptide inhibitor of DNA replication defines the site of interaction between the cyclin–dependent kinase inhibitor p21–$^{WAF1}$ and proliferating cell nuclear antigen" Current Biology, vol. 5 No. 3, (1995) pp. 275–282.

Waga, S., et al., "The p21 inhibitor of cyclin–dependent kinases controls DNA replication by interaction with PCNA" Nature, vol. 369, (Jun. 16, 1994) pp. 574–578.

Nakanishi, M., et al. "Identification of the active region of the DNA synthesis inhibitory gene p21$^{Sdi1/CIP1/WAF1}$", The EMBO Jour. 14(3):555–563 (1995).

Chen, I., et al., "Characteriztion of p21$^{Cip1/Waf1}$ peptide domains required for cyclin E/Cdk2 and PCNA interaction", Oncogene 12:595–607 (1996).

Ball, K., et al., "Human and plant proliferating–cell nuclear antigen have a highly conserved binding site for the p53–inducible gene product p21$^{WAF1}$", Eur. J. Biochem. 237:854–861 (1996).

Eastham, J., et al., "In Vivo Gene Therapy with p53 or p21 Adenovirus for Prostate Cancer", Cancer Research 55:5151–5155 (1995).

Chen J., et al., "Separate domains of p21 involved in the inhibition of Cdk kinase and PCNA", Nature 374:386–388 (1995).

Harper, J., et al., "Inhibition of Cyclin–dependent Kinases by p21", Mol. Biol. of the Cell 6:387–400 (1995).

Luo, Y., et al., "Cell–cycle inhibition by independent CDK and PCNA binding domains in p21$^{Cip1}$", Nature 375:159–161 (1995).

Nakanishi, M., et al., "The C–terminal Region of p21$^{SDI1/WAF1/CIP1}$ is Involved in Proliferating Cell Nuclear Antigen Binding but Does Not Appear to Be Required for Growth Inhibition", The Jour. of Biol. Chem. 270(29):17060–17063 (1995).

(List continued on next page.)

Primary Examiner—Sheela Huff
(74) Attorney, Agent, or Firm—Lahive & Cockfield, LLP; Amy E. Mandragouras, Esq.; Giulio A. DeConti, Jr., Esq.

(57) ABSTRACT

Substances are disclosed which have the property of binding to PCNA, the substances comprising (i) a fragment of the p21$^{WAF1}$ protein including residues 141 to 160 of the p21$^{WAF1}$ amino acid sequence, or an active portion or derivative thereof; or (ii) functional mimetics of these protein fragments. In particular, the PCNA binding activity is shown to lie within the sequence motif OTSMTDFY, with the residues shown in bold being critical for PCNA binding, with those underlined being important. These substances are useful in the treatments of disorders in which PCNA is implicated, e.g. hyperproliferative disorders such as cancer and psoriasis, the substances binding to PCNA to inactivate it or functionally deplete its level. Also disclosed is the use of a yeast two hybrid screening technique for screening candidate peptides for binding to PCNA.

16 Claims, 11 Drawing Sheets

OTHER PUBLICATIONS

Goubin, F., et al., "Identification of binding domains on the p21$^{Cip1}$ cyclin–dependent kinase inhibitor", *Oncogene* 10:2281–2287 (1995).

El–Deiry, W., et al., "WAF1, a Potential Mediator of p53 Tumor Suppression", *Cell* 75:817–825 (1993).

Gu, Y., et al., "Inhibition of CDK2 activity in vivo by an associated 20K regulatory subunit", *Nature* 366:707–710 (1993).

Deng, C., et al., "Mice Lacking p21$^{CIP1/WAF1}$ Undergo Normal Development, but Are Defective in G1 Checkpoint Control", *Cell* 82:675–684 (1995).

Waldman, T., et al., "p21 is Necessary for the p53–mediated $G_1$ Arrest in Human Cancer Cells", *Cancer Research* 55:5187–5190 (1995).

Su, J., et al., "Cloning and characterization of the Xenopus cyclin–dependent kinase inhibitor p27$^{XIC1}$", *Proc. Natl. Acad. Sci. USA* 92:10187–10191 (1995).

Zhang, H., et al., "p21–containing cyclin kinases exist in both active and inactive states", *Genes & Devel.* 8:1750–1758 (1994).

Chen, J., et al., "Cyclin–Binding Motifs Are Essential for the Function of p21$^{CIP1}$", *Mol. Cell. Biol.* 16(9):4673–4682 (1996).

Lin, J., et al., "Analysis of Wild–Type and Mutant p21$^{WAF-1}$ Gene Activities", *Mol. Cell. Biol.* 16(4):1786–1793 (1996).

Dulić, V., et al., "p53–Dependent Inhibition of Cyclin–Dependent Kinase Activities in Human Fibroblasts during Radiation–Induced G1 Arrest", *Cell* 76:1013–1023 (1994).

Bravo, R., et al., "Cyclin/PCNA is the auxiliary protein of DNA polymerase–δ", *Nature* 326:515–517 (1987).

Prelich, G., et al., "Functional identity of proliferating cell nuclear antigen and a DNA polymerase–δ auxiliary protein", *Nature* 326:517–520 (1987).

Fields, S., et al., "A novel genetic system to detect protein–protein interactions", *Nature* 340:245–246 (1989).

Durfee, T., et al., "The retinoblastoma protein associates with the protein phosphatase type 1 catalytic subunit", *Genes & Devel.* 7:555–569 (1993).

Polyak, K., et al., "Cloning of p27$^{Kip1}$, a Cyclin–Dependent Kinase Inhibitor and a Potential Mediator of Extracellular Antimitogenic Signals", *Cell* 78:59–66 (1994).

Toyoshima, H., et al., "p27, a Novel Inhibitor of G1 Cyclin–Cdk Protein Kinase Activity, is Related to p21", *Cell* 78:67–74 (1994).

Waseem, H., et al., "Isolation and analysis of the fission yeast gene encoding polymerase δ accessory protein PCNA", *The EMBO Jour.* 11(13):5111–5120 (1992).

Kong, X.–P., et al., "Three–Dimensional Structure of the β Subunit of E. coli DNA Polymerase III Holoenzyme: A Sliding DNA Clamp", *Cell* 69:425–437 (1992).

Picksley, S., et al., "Immunochemical analysis of the interaction of p53 with MDM2;—fine mapping of the MDM2 binding site on p53 using synthetic peptides", *Oncogene* 9:2523–2529 (1994).

Roos, G., et al., "Analysis of the Epitopes of Proliferating Cell Nuclear Antigen Recognized by Monoclonal Antibodies", *Lab. Inves.* 68(2):204–210 (1993).

Churchill, M., et al., "Crystal Structure of a Peptide Complex of Anti–influenza Peptide Antibody Fab 26/9", *J. Mol. Biol.* 241:534–556 (1994).

Melendy, T., et al., "Purification of DNA Polymerase δ as an Essential Simian Virus 40 DNA Replication Factor", *The Jour. of Biol. Chem.* 266(3):1942–1949 (1991).

Waseem, N., et al., "Monoclonal antibody analysis of the proliferating cell nuclear antigen (PCNA): Stuctural Conservation and the Detection of a Nucleolar Form", *Jour. of Cell Sci.* 96:121–129 (1990).

Breeden, L., et al., "Regulation of the Yeast HO Gene", Cold Spring Harbor Symp. Quant. Biol. 50:643–650 (1985).

Hunter, T., "Braking the Cycle", *Cell* 75:839–841 (1993).

Noda, A., et al., "Cloning of Senescent Cell–Derived Inhibitors of DNA Synthesis Using an Expression Screen", *Exper. Cell Res.* 211:90–98 (1994).

Wang, E., et al., "The Murine p53 Protein Blocks Replication of SV40 DNA In Vitro by Inhibiting the Initiation Functions of SV40 Large T Antigen", *Cell* 57:379–392 (1989).

Basi, G., et al., "TATA box mutations in the *Schizosaccharomyces pombe* nmt1 promoter affect transcription efficiency but not the transcription start point or thiamine repressibility", *Gene* 123:131–136 (1993).

Hoffman, C., et al., "A ten–minute DNA preparation from yeast efficiently releases autonomous plasmids for transformation of *Escherichia coli*", *Gene* 57:267–272 (1987).

Gietz, D., et al., "Improved method for high efficiency transformation of intact yeast cells", *Nucleic Acids Res.* 20(6):1425 (1992).

FIG. 4A

| | | | | | | | | | | | | | | | | | |
|---|---|---|---|---|---|---|---|---|---|---|---|---|---|---|---|---|---|
| Peptide 1. | M | S | E | P | A | G | D | V | R | Q | N | P | C | G | S | K | A C R R |
| Peptide 2. | K | A | C | R | R | L | F | G | P | V | D | S | E | Q | L | S | R D C D |
| Peptide 3. | S | R | D | C | D | A | L | M | A | G | C | I | Q | E | A | R | E R W N |
| Peptide 4. | R | E | R | W | N | F | D | F | V | T | E | T | P | L | E | G | D F A W |
| Peptide 5. | G | D | F | A | W | E | R | V | R | G | L | G | L | P | K | L | Y L P T |
| Peptide 6. | L | Y | L | P | T | G | P | R | R | G | R | D | E | L | G | G | G R R P |
| Peptide 7. | G | G | R | R | P | G | T | S | P | A | L | L | Q | G | T | A | E E D H |
| Peptide 8. | A | E | E | D | H | V | D | L | S | L | S | C | T | L | V | P | R S G E |
| Peptide 9. | P | R | S | G | E | Q | A | E | G | S | P | G | G | P | G | D | S Q G R |
| Peptide 10. | K | R | R | Q | T | S | M | T | D | F | Y | H | S | K | R | R | L I F S |
| Peptide 11. | T | S | M | T | D | F | Y | H | S | K | R | R | L | I | F | S | K R K P |
| | | | | | | | | | | | | | | | | | |
| Peptide 63. | L | K | Y | Y | L | A | P | K | I | E | D | E | E | G | S | | |

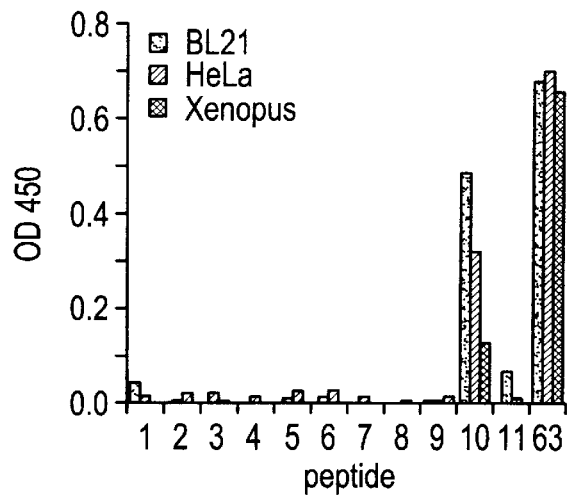

FIG. 4B

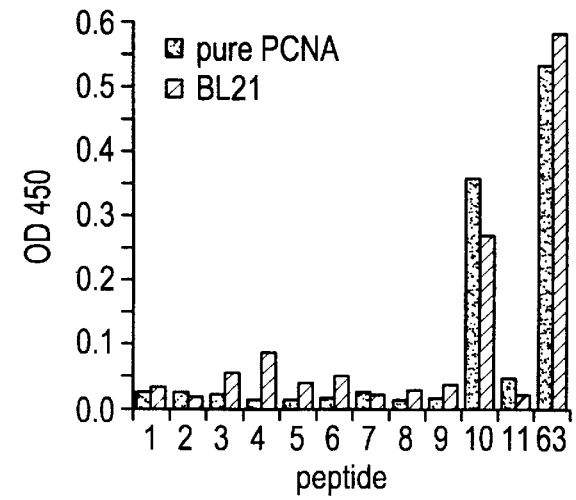

| | |
|---|---|
| 65 | PRSGEQAEGSPGGPGDSQGR |
| 66 | EQAEGSPGGPGDSQGRKRRQ |
| 67 | GSPGGPGDSQGRKRRQTSMT |
| 68 | GPGDSQGRKRRQTSMTDFYH |
| 69 | SQGRKRRQTSMTDFYHSKRR |
| 70 | KRRQTSMTDFYHSKRRLIFS |
| 71 | TSMTDFYHSKRRLIFSKRKP |
| 20 | DFYHSKRRLIFSKRKPGDS |

IDENTIFICATION OF THE P21$_{WAF1}$-PCNA INTERACTION SITE AND THERAPEUTIC APPLICATIONS THEREOF

FIELD OF THE INVENTION

The present invention relates to the area of cancer therapeutics. More particularly, the present invention relates to the identification of the region of p21$^{WAF1}$ responsible for binding to proliferating cell nuclear antigen (PCNA) and substances, fragments and mimetics based on this region. The present invention also relates to pharmaceutical compositions comprising these molecules and their use in therapeutic applications for inhibiting DNA replication or binding of PCNA, for example in tumour and other hyperproliferative cells.

BACKGROUND OF THE INVENTION p21$^{WAF1}$ is a protein that may be transcriptionally induced by the tumour suppression protein p53 and acts as a potent inhibitor of cyclin dependent kinases (Cdks) in G1 and S phases of the cell cycle. Thus, p21$^{WAF1}$ acts as a regulator of the cell cycle in response to activation of the p53 checkpoint pathway at least in part by inhibiting Cdk activity (1–3). p21$^{WAf1}$ is also known as p21$^{CIP1}$ (9) p21$^{Pic}$ (33) p20$^{CAP}$ (34) and Sdi1 (35).

Complexes between p21$^{WAF1}$ and Cdks can exist in both catalytically active and inactive forms, suggesting that the regulation is a subtle effect (4). p21$^{WAF1}$ has also been reported to bind to PCNA at high concentration in vitro and block DNA replication (5). PCNA is a processivity factor for polymerase δ which plays an essential role in DNA replication and repair (6, 7). In transformed cell lines, p21$^{WAF1}$ expression is depressed, and cyclin dependent kinases are found in a Cdk/cyclin binary state, rather than in Cdk/Cyclin/p21$^{WAF1}$/PCNA complexes, although the stoichiometry of these complexes is not clear (1, 8–10). Thus, it appears that during p53-mediated suppression of cell proliferation, p21$^{WAF1}$ is important for co-ordinating cell cycle progression, DNA replication and repair of damaged DNA.

SUMMARY OF THE INVENTION

We have now found that p21$^{WAF1}$ interacts with PCNA in vivo and at concentrations far lower than those reported previously. The mapping of the region of p21$^{WAF1}$ that is responsible for the interaction with PCNA is also disclosed. In particular, the applicants have found that peptides derived from the C-terminal region of p21$^{WAF1}$ bind to PCNA and have shown that this accounts for the inhibition of DNA replication. The interaction of p21$^{WAF1}$ with cyclin-Cdks and PCNA provides the possibility of using p21$^{WAF1}$ to co-ordinate cell proliferation and cell cycle control.

The applicants used a yeast two hybrid screening technique to establish an in vivo interaction between the C-terminal part of p21$^{WAF1}$ and PCNA. In particular, analysis of a series of overlapping peptides representing the protein sequence of p21$^{WAF1}$ identified a 20 amino acid peptide (residues 141–160) which showed high affinity and selectivity of binding to PCNA, and also inhibited SV40 DNA replication in vitro in a concentration-dependent manner. Further experiments have shown that residues essential for PCNA binding and inhibition lie within the motif defined by the sequence QTSMTDFY (SEQ ID NO:1).

This high affinity of the interaction between PCNA (from both normal and tumour cells) and the p21$^{WAF1}$ peptide means that it is possible to use these peptides, or fragments or mimetics thereof, in tumour therapy and in the treatment of hyperproliferative diseases in which PCNA is implicated, eg cancer or psoriasis.

Accordingly, in one aspect, the present invention provides a substance which has the property of binding to PCNA, said substance comprising:

(i) a fragment of the p21$^{WAF1}$ protein including residues 141 to 160 of the p21$^{WAF1}$ amino acid sequence, or an active portion or derivative thereof; or, (ii) a functional mimetic of said protein fragment.

In the present invention, "an active portion" means a peptide which is less than said full length p21$^{WAF1}$ amino acid sequence, but which retains the property of binding to PCNA.

In the present invention, "functional mimetic" means a substance which may not contain an active portion of the p21$^{WAF1}$ amino acid sequence, and probably is not a peptide at all, but which has the property of binding to PCNA.

In the present invention, "a derivative" means a fragment of the p21$^{WAF1}$ protein modified by varying the amino acid sequence of the protein, eg by manipulation of the nucleic acid encoding the protein or by altering the protein itself. Such derivatives of the natural amino acid sequence may involve insertion, addition, deletion or substitution of one or more amino acids, without fundamentally altering the essential activity of the protein.

Preferably, the fragment of the p21$^{WAF1}$ protein includes residues 144 to 151 of the p21$^{WAF1}$ amino acid sequence these residues defining a sequence motif QTSMTDFY (SEQ ID NO:1), where residues shown in bold are critical for PCNA binding, and those underlined are important.

Thus, in one embodiment, the present invention provides a class of peptides based on the C-terminal region of p21$^{WAF1}$. These compounds may be useful in the preparation of pharmaceuticals for treating conditions in which PCNA is implicated, including hyperproliferative diseases, such as cancer and psoriasis. These peptides preferably include the sequence motif KRRQTSMTDFYHSKRRLIFS (SEQ ID NO:2), as shown in FIG. 4b, or still more preferably, the sequence motif QTSMTDFY (SEQ ID NO:1), and functional variants or mimetics of these peptides.

In a further aspect, the present invention provides pharmaceutical compositions for inhibiting DNA replication and/or binding PCNA comprising one or more of the above peptides or mimetics. Optionally, the pharmaceutical compositions comprise one or more of the above substances in combination with a physiologically acceptable carrier.

In a further aspect, the present invention provides the peptides, mimetics and compositions described above for use in methods of medical treatment, such as inactivating or functionally depleting PCNA in cells, especially tumour cells.

In a further aspect, the present invention uses a method of screening polypeptides for binding to PCNA comprising:

(i) transforming yeast cells with a vector capable of expressing a fusion of the DNA binding domain of Gal4 and PCNA, the yeast cells being capable of expressing one or more reporter constructs under the control of the Gal1 promoter;

(ii) transforming said yeast cells with one or more vectors capable of expressing a fusion of the activation domain of Gal4 and a given candidate polypeptide; and, (iii) detecting the production of the reporter constructs caused when the candidate polypeptide binds to PCNA, thereby reconstituting the Gal4 transcriptional activity.

This method is used below to detect the interaction between artificially synthesised peptides and PCNA to define the PCNA binding site in p21$^{WAF1}$ more specifically. However, it could readily be used to screen candidate peptides, eg mimetics, for PCNA binding activity.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, eg peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, eg by substituting each residue in turn. These parts or residues constituting the active region of the compound are known as its "pharmacophore".

Once the pharmacophore has been found, its structure is modelled according to its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The plasmid pas-pcnahs was constructed which expresses a hybrid protein between the DNA binding domain of Gal4 (amino acids 1–147; Gal4$^{AS}$) and human PCNA (13). This plasmid was transformed into the S.cerevisiae strain Y190 that expresses the reporter genes lacz (*E.coli*) and HIS3 (*S.cerevisiae*) under the control of the GAL1 promoter (30). The resulting transformants did not activate either of the reporter constructs in this strain; lacZ (as determined by a filter lift assay for β-galactosidase (31) or HIS3 (assayed by growth on SDA (SD plus adenine) supplemented with leucine and containing 50 mM 3 -aminotriazole) (14). This transformant strain was then itself transformed with a human cDNA library in the vector pACT where cDNAs are expressed as fusion constructs with the activation domain of Gal4 (amino acids 768–881) (12).

Tranformants containing library-encoded PCNA interacting proteins (Pips) result in the re-constitution of Gal4 activity, and thus in the expression of reporter constructs. These were selected for by plating on SDA containing 3-aminotriazole, while an aliquot was plated on SDA without 3-aminotriazole to determine transformation frequency. Putative positives were tested for lacZ expression as described above, then were streaked out on SDA containing 3-aminotriazole, and a single colony isolated for further analysis. cDNA library plasmids were rescued into *E.coli* strain JA226 (32).

Figure 2:
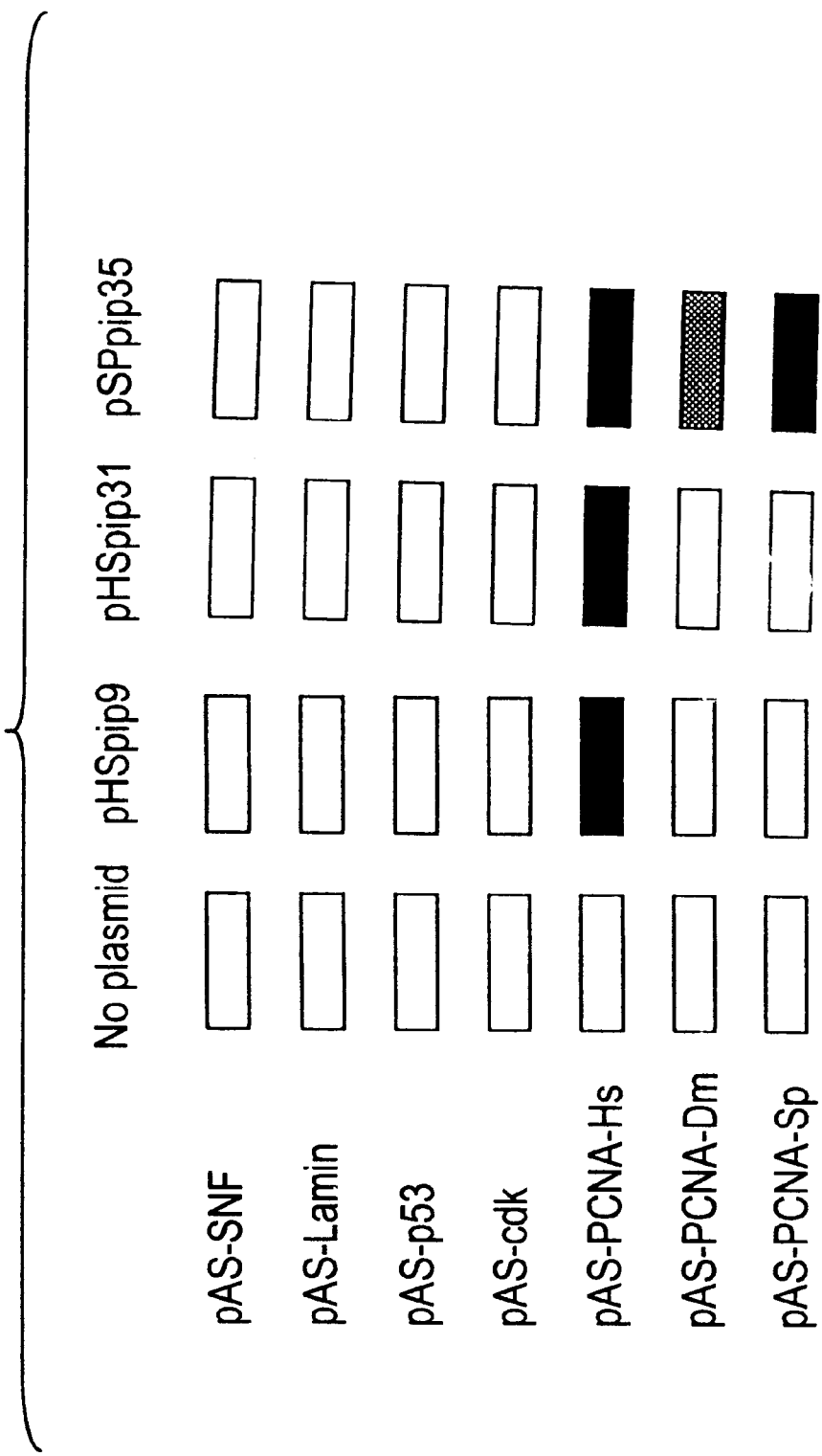

FIG. 2: Summary of two hybrid screening results.

Bars indicate the result of β-galactosidase colony lift assays performed upon transformant strains, as indicated by plasmids named on the horizontal and vertical axes. pHSpip9 and pHSpip31 encode Gal4-p21$^{WAF1}$ fusions as described in the text. pSPpip35 encodes the Gal4$^{ACT}$ domain fused to upstream sequences of the *S.pombe* PCNA gene pcn1$^{30}$ so that pcn1$^{30}$ is expressed in-frame.

All transformants were also streaked out on SDA containing appropriate supplements and 3-aminotriazole to test for His3 expression. Only transformants which were positive in both tests were counted as true positives. Black bars indicate a strongly positive result from both tests, the shaded bar indicates a weak positive and white bars indicate a negative result. The pAS-pcna plasmids contain the entire open reading frame of PCNA from *Homo sapiens* (Hs), *Drosophila melanogaster* (Dm) and *Schizosaccharomyces pombe* (Sp) respectively in the vector pAS2. The control plasmids pAS-SNF1, pAS-p53, pAS lamin and pAS-CDK2 are as described by Harper et al., (9).

Figure 3:
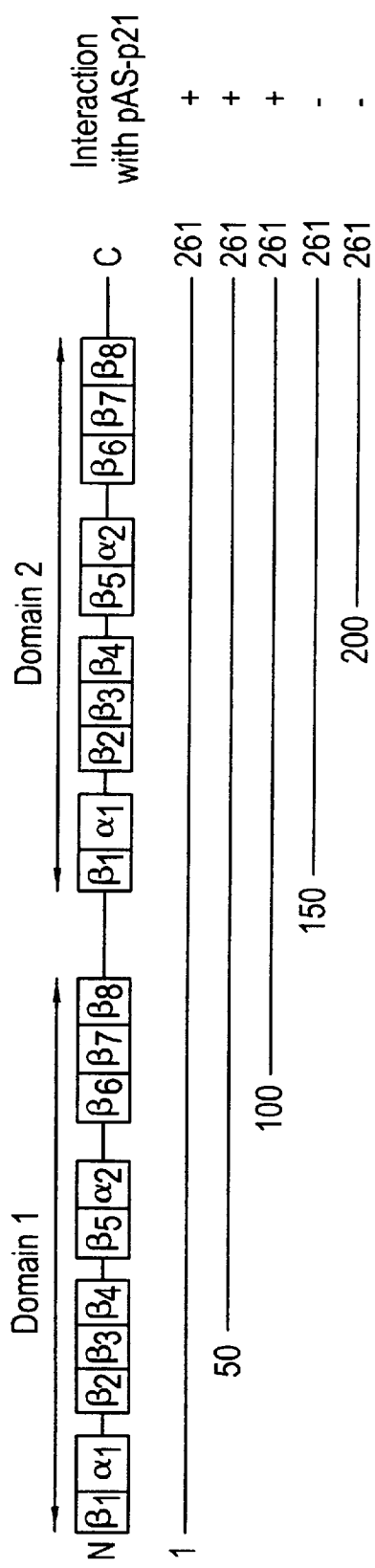

FIG. 3: Identification of p21$^{WAF1}$ interacting regions in PCNA.

Schematic diagram indicating structural domains within the PCNA molecule. Numbers indicate β-sheet domains, and α-helices as suggested by Kong et al., (18). Bars below indicate the regions of PCNA expressed as fusions with Gal4$^{ACT}$ and the column on the right (+/−) indicates a positive/negative result when tested for interaction with p21$^{WAF1}$ in the two hybrid system (32).

FIGS. 4(a–c): Peptides of p21$^{WAF1}$ and pepscan analysis of PCNA binding.

(a) Peptides 1–11 represent the entire protein sequence of p21$^{WAF1}$ (1), with overlaps between adjacent peptides. Peptide 63 represents the C-terminal 15 amino acids of PCNA. (b & c) p21$^{WAF1}$ peptides were incubated on streptavidin-coated ELISA dishes, the plates were washed thoroughly then cell extracts from HeLa, *Xenopus* or *E.coli* BL21 overexpressing PCNA were added (b). In (c), purified human PCNA from BL21 was compared with crude lysate of these cells on the same peptide array in ELISA. After extensive washing, bound PCNA was detected using polyclonal anti-PCNA antibody 3009 followed by HRP-conjugated anti-rabbit secondary antibody and TMB visualisation. Optical density at 450 nm was measured.

Figure 5A:
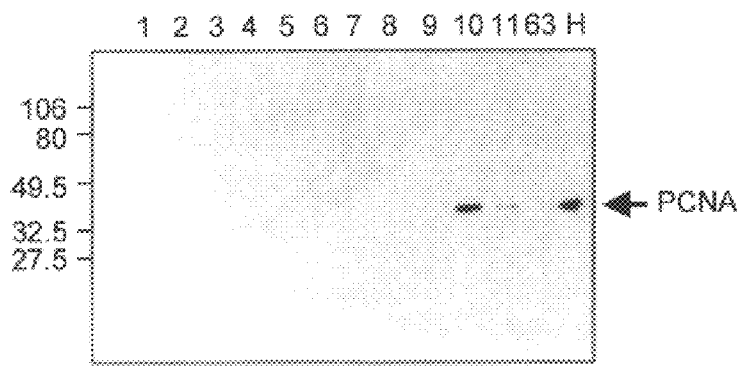

FIGS. 5(a–c). Mapping sites of p21$^{WAF1}$ required for PCNA binding using precipitation analysis.

(a) All 11 peptides of p21$^{WAF1}$ separately attached to streptavidin-agarose beads were incubated in HeLa cell extract then beads were separated from the lysate by centrifugation. Bound proteins were analysed by SDS-PAGE followed by Western blotting with PC10 monoclonal anti-PCNA antibody followed by HRP-anti-mouse secondary antibody and ECL detection. Peptides are numbered as in FIG. 4a; H represents undepleted HeLa extract. Molecular weight marker sizes are shown in kDa. The position of PCNA is marked by an arrow. (b) Western blot probed with monoclonal antibody PC10 and (c) Coomassie stained gel of a peptide 10-streptavidin bead precipitation from extracts of various human tumour cell lines (the results from seven out of fourteen lines tested are shown): A431 (sample 1), HOS (sample 2), SKBR3 (sample 3), BT549 (sample 4), MDA231 (sample 5), T47D (sample 6) and DLD1 (sample 7). "s" indicates supernatant after incubation with peptide-10 beads, and "b" contains proteins precipitated by the peptide-10-streptavidin agarose beads. "M" shows position of molecular weight standards and sizes are given in kDa.

Figure 6A:
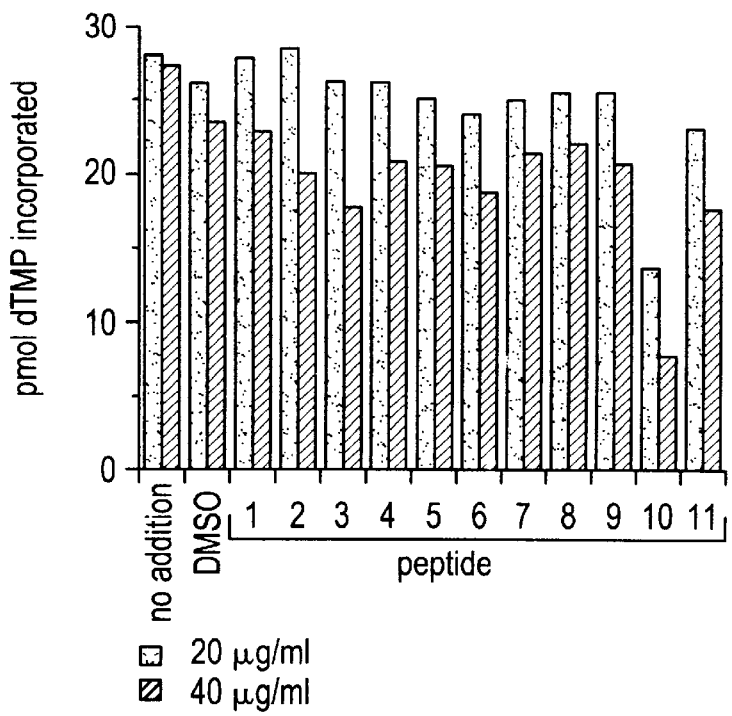

FIGS. 6(a–b): Inhibition of DNA replication by peptide 10.

(a) All peptides of p21$^{WAF1}$ were added to an in vitro SV40 replication reaction to a final concentration of 20 ng/µl (hatched columns) or 40 ng/µl (filled columns), compared with DMSO at equivalent dilution to the 40 ng/µl peptide samples, or with no addition. After 2 hours' incubation at 37° C., incorporation o³f H-dTMP was measured by TCA precipitation and scintillation counting. (b) Peptide 10 was added to the replication reaction at a range of concentrations up to 30 ng/µl, compared with equivalent dilutions of the peptide solvent DMSO. Extent of label incorporation was analysed after two hours as above. The same concentrations of peptide 9 (data not shown) or the solvent alone had no appreciable effect on levels of DNA synthesis.

FIGS. 7(a–c). Determination of minimal binding site of PCNA on p21$^{WAF1}$ (a) Peptides were generated from the p21$^{WAF1}$ sequence with amino acid overlaps and 4 amino acid overhangs to cover the putative PCNA binding site defined above. (b) These peptides were tested for ability to bind to PCNA in ELISA, as in FIG. 4. (c) The peptides were individually analysed for ability to inhibit SV40 DNA replication in vitro by adding the peptide at the start of the replication reaction. Incubations were carried out for 2 h at 37° C. and incorporation of $^3$H-dTMP measured by TCA precipitation and filter binding.

Figure 8A:
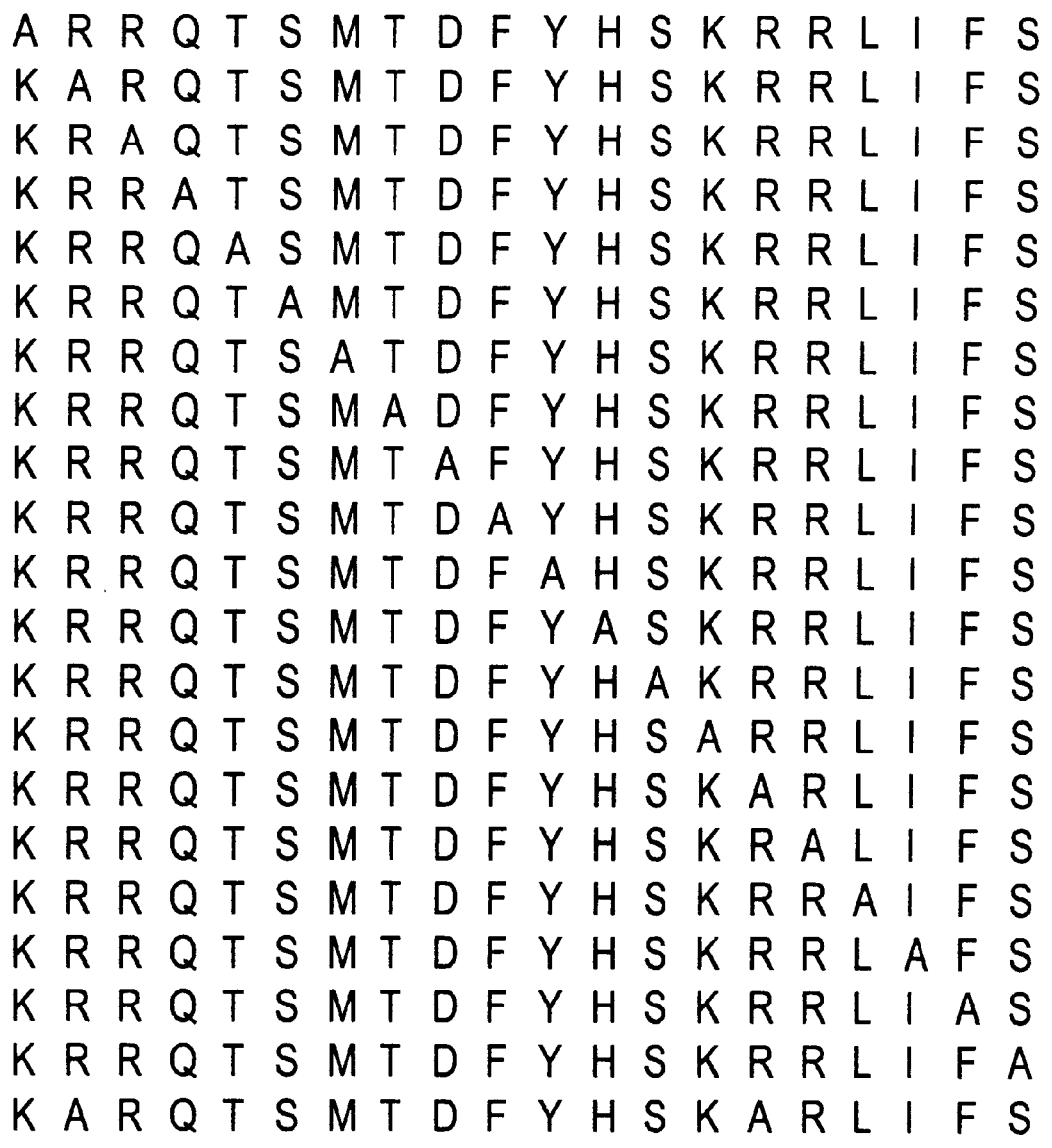

FIGS. 8(a–c). Alanine scanning of peptide 10.

(a) Each amino acid in the putative PCNA binding site of p21$^{WAF1}$ (peptide 10) was sequentially changed to alanine ("44 "–"63") and in peptide "64 " two arginines were altered to alanine within the same peptide. (b) Pepscan ELISA to determine PCNA binding capacity of each of the peptides using bacterially expressed human PCNA detected with polyclonal antibody 3009. (c) Effect of the peptides on SV40 DNA replication in vitro (as in FIG. 7c).

The following examples in the detailed description are provided to exemplify various aspects of the invention and are not intended to limit the scope of the invention.

DETAILED DESCRIPTION

Figure 1:
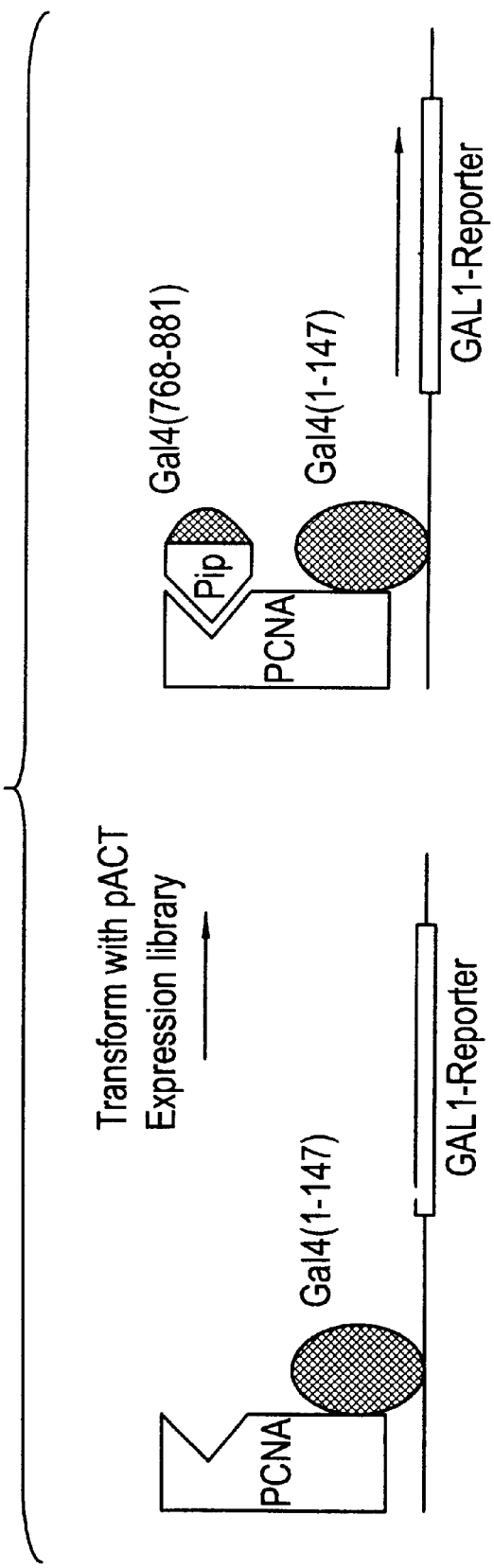
FIG. 1: Strategy for detecting PCNA Interacting Proteins (pips) using the two hybrid system.

The applicants screened for proteins that physically interact with human PCNA using a two-hybrid interaction trap system that detects polypeptide interactions via the reconstitution of a functional transcriptional activator in the yeast Saccharomyces cerevisiae (11, 12). A plasmid that expresses a hybrid protein between the DNA binding domain of Gal4 (Gal4$^{AS}$) and human PCNA (13) was used to screen plasmids expressing hybrid fusion constructs between DNA molecules from a human cDNA library and the DNA encoding the transcriptional activation domain of Gal4 (Gal4$^{ACT}$) (FIG. 1) (12). 77 His$^{30}$ colonies were picked from over 1×10$^6$ transformants of which 14 expressed β-galactosidase. pACT-derived library plasmids were isolated from 12 of these strains which re-tested positive upon co-transformation with pAS-pcnahs (14). Each plasmid encoding Human PCNA interacting protein (pHSpip) was tested for non-specific interactions with other Gal4$^{AS}$ fusions by co-transforming with various pAS plasmids (FIG. 2), and the plasmids were grouped according to cross-hybridisation and DNA sequence analysis. Each pHSpip was also tested for interactions with both Drosophila melanogaster and Schizosaccharomyces pombe PCNA. The 12 positives fell into three classes. One class (pHSpip9 and pHSpip31) showed a specific interaction with pAS-pcnahs. Sequence analysis indicated that these plasmids both expressed the C-terminal 89 amino acids of p21$^{WAF1}$ (8–10) in frame with Gal4$^{ACT}$ although the vector sequences of one of the plasmids showed a slight re-arrangement. Thus, the C-terminal half of p21$^{WAF1}$ is sufficient for interaction with PCNA.

Previously, clones encoding full length p21$^{WAF1}$ have been shown to interact in the two-hybrid system with human Cdk2 (9). Neither of the p21$^{WAF1}$ clones identified here reacted positively with human Cdk2 in a two-hybrid assay, suggesting that the interaction between p21$^{WAF1}$ and Cdk2 is dependent upon the amino-terminal half of p21$^{WAF1}$. In support of this, the Cdk inhibitor p21$^{kiP1}$ has a region of sequence similarity to an N-terminal region of p21$^{WAF1}$, and a 52 amino acid peptide (Kip1 [28–29]) corresponding to this region retains Cdk inhibitory activity (15, 16).

A similar screen was undertaken to search for S.pombe cDNAs encoding proteins that would interact with S.pombe PCNA (pcn1$^+$) (17). Two of the clones identified expressed the entire open reading frame of pcn1$^-$, suggesting that PCNA is able to interact with itself. These results support the model proposed by Kong et al (18) in which PCNA forms a homo-trimer which acts as a sliding clamp tethering the replication complex to the DNA strand. Furthermore, pcn1$^+$ was found to interact with both human and D.melanogaster PCNA, suggesting that the interaction is evolutionarily conserved (FIG. 2). Human PCNA has sufficient DNA binding capacity for a PCNA-Gal4$^{ACT}$ hybrid to activate reporter gene expression in the two hybrid system, so such a construct could not be used for two-hybrid interaction analysis.

p21$^{WAF1}$ interacts with the central region of PCNA

A series of C-terminal deletion constructs of human PCNA fused to Gal4$^{AS}$ were then tested to identify regions of PCNA that interact with p21$^{WAF1}$ in the two-hybrid assay (13). The results of these experiments (FIG. 3) suggest that p21$^{WAF1}$ interacts with a central region of PCNA. Structural and sequence similarities between the β subunit of DNA polymerase III in E.coli have suggested a model in which three PCNA molecules, each consisting of two repeated domains, form a toroid structure which encircles the DNA strand (18). The data in FIG. 3 are consistent with p21$^{WAF1}$ interacting with the "junctional loop" which connects the two domains.

Peptide mapping of sites on p21$^{WAF1}$ important for interaction with PCNA

In order to refine the map of the site(s) on p21$^{WAF1}$ that interact with PCNA, the binding capability of a series of 11 overlapping 20-mer peptides representing the p21$^{WAF1}$ sequence were tested (FIG. 4a) (19). This approach has been used successfully to fine-map protein-protein interactions (e.g. p53-MDM2) and antibody epitopes (20–22).

The p21$^{WAF1}$ peptides were linked to biotin, permitting attachment to streptavidin-coated ELISA plates. PCNA from various sources, including HeLa cell extract, Xenopus egg extract and lysate of E. coli BL21 overexpressing a human PCNA clone (23), were applied to the immobilised peptide array. Bound PCNA was detected using either polyclonal antibody 3009 that recognises the C-terminal 15 amino acids of native and denatured PCNA (24, 25). PCNA from the three sources tested binds with great specificity to peptide 10 of sequence KRRQTSMTDFYHSKRRLIFS (SEQ ID NO:2) (FIG. 4b). The interaction of PCNA with the adjacent peptide 11, that shares all but the initial four residues, is much weaker (13% of binding to peptide 10 for bacterially expressed PCNA and only 3.8% for HeLa PCNA).

Similar results were obtained with monoclonal antibody PC10 (26) demonstrating that the interaction between PCNA and peptide 10 of $p21^{WAF1}$ is specific to PCNA and not due to antibody cross-reaction. This specificity was confirmed using purified PCNA (27) which bound strongly and specifically to peptide 10 of $p21^{WAF1}$ (FIG. 4c).

$p21^{WAF1}$ peptides can precipitate PCNA from cell extracts

Figure 5B:
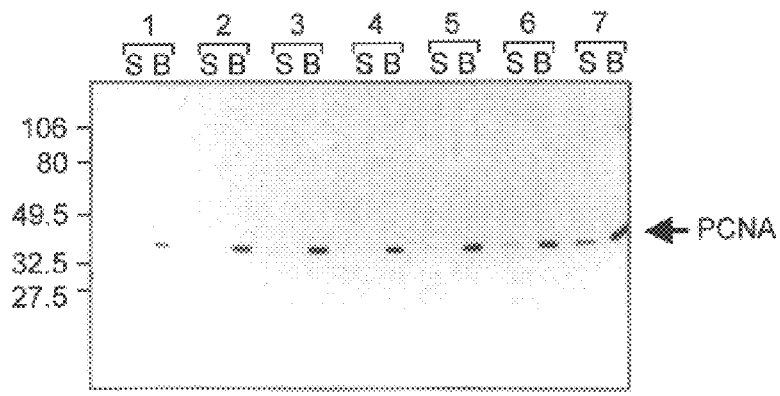
Figure 5C:
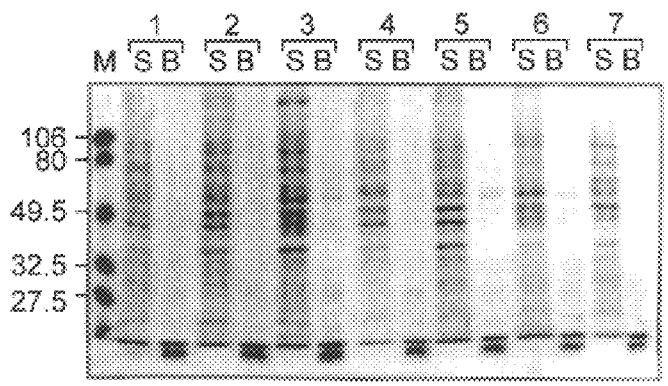

To confirm the specificity of the interaction between native PCNA and $p21^{WAF1}$ peptides further, the peptides were attached to streptavidin-agarose beads and incubated in HeLa cell extract. The proteins that were subsequently precipitated were separated electrophoretically, blotted onto nitrocellulose, and probed with anti-PCNA monoclonal antibody PC10 (FIG. 5a) (28): PCNA was precipitated by beads carrying peptide 10, and also weakly by peptide 11. The peptide 10 precipitate contained a similar amount of PCNA as the untreated control extract (HeLa), suggesting a highly efficient capture of soluble PCNA. PCNA was not detected in the precipitates of any other $p21^{WAF1}$ peptide. PCNA could be quantitatively removed from extracts of 14 other human tumour cell lines by peptide 10 beads (FIG. 5b). In some cases, e.g. SKBR3 and BTS549 cells, there was almost complete transfer of PCNA from the cell lysate to the beads. This suggests that PCNA from these tumour cell lines is not altered in its capacity to bind $p21^{WAF1}$. Parallel gels stained with Coomassie brilliant blue show that the interaction with PCNA is highly specific, as the amount of total protein precipitating with the beads is negligible (FIG. 5c). The interaction of PCNA with the $p21^{WAF1}$ peptide 10 beads could not be disrupted using 100 mM glycine pH 2.5, 100 mM triethylamine pH 12.5 or 1.4 M NaCl in batch elution tests, demonstrating the strength of the binding. Strong binding could still be detected when only 500 pg of peptide was applied to the wells in the ELISA assay. These results suggest that peptide 10 beads may be used to deplete cell extracts of PCNA, and should therefore prove to be a useful tool in further elucidating the action of PCNA in DNA replication and repair.

Inhibition of SV40 DNA replication by $p21^{WAF1}$ peptide 10

Figure 6B:
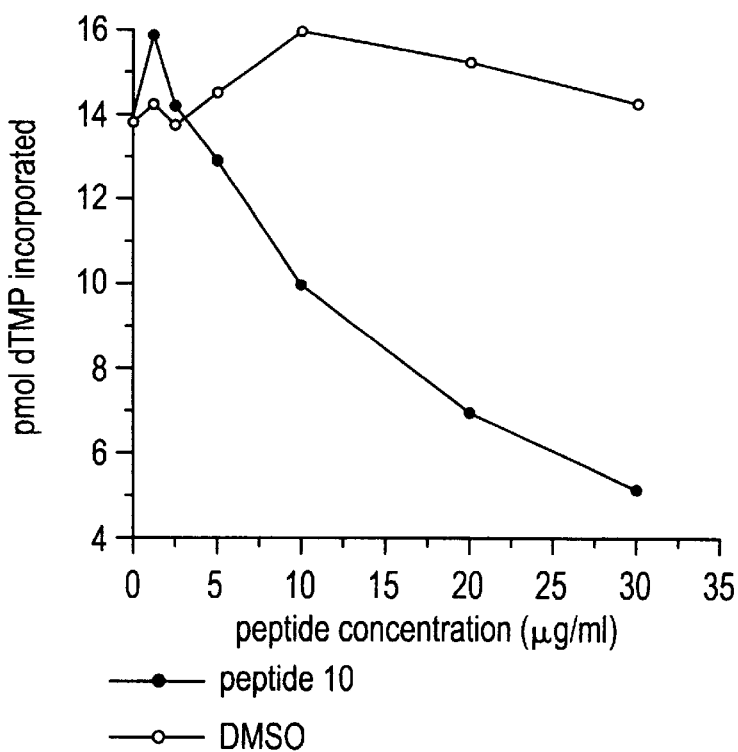

$p21^{WAF1}$ has recently been reported to bind PCNA and to inhibit the replication of SV40 DNA (5). Therefore, we examined the 20-mer peptides for their effect on SV40 DNA replication in vitro (FIG. 6a) (29). Of all the peptides, only peptide 10 had a significant effect on DNA replication, reducing incorporation of $^3$H-dTMP to 51% of control levels at 20 ng/µl and to 31% of control values at 40 ng/µl. The concentration dependence of the inhibition of replication by peptide 10 is shown in FIG. 6b. For a peptide, the activity is remarkably high, requiring only a ten-fold higher molar ratio than full length $p21^{WAF1}$ protein. Accordingly, these peptides which are capable of inhibiting DNA replication and/or binding to PCNA in cells may have important therapeutic applications in the treatment of tumours and other hyperproliferative diseases, such as cancer and psoriasis.

Further identification of the PCNA binding region of $p21^{WAF1}$

Figure 7B:
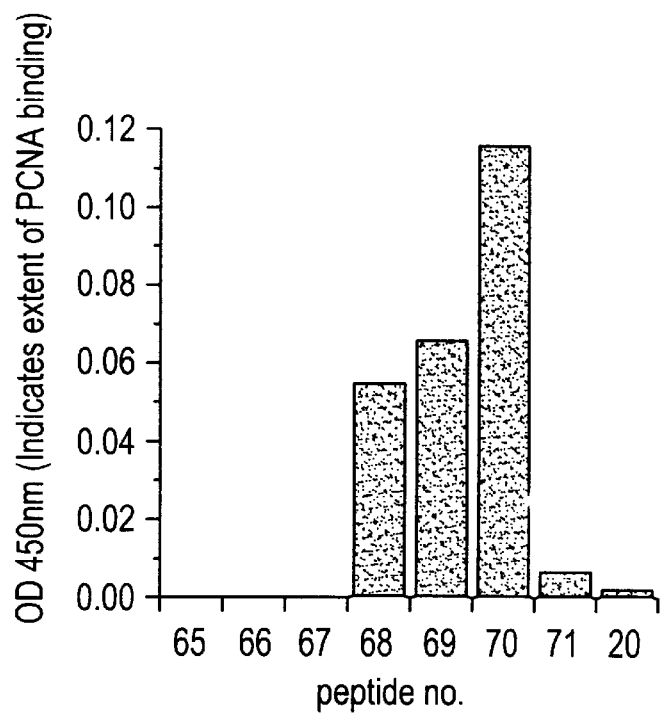
Figure 7C:
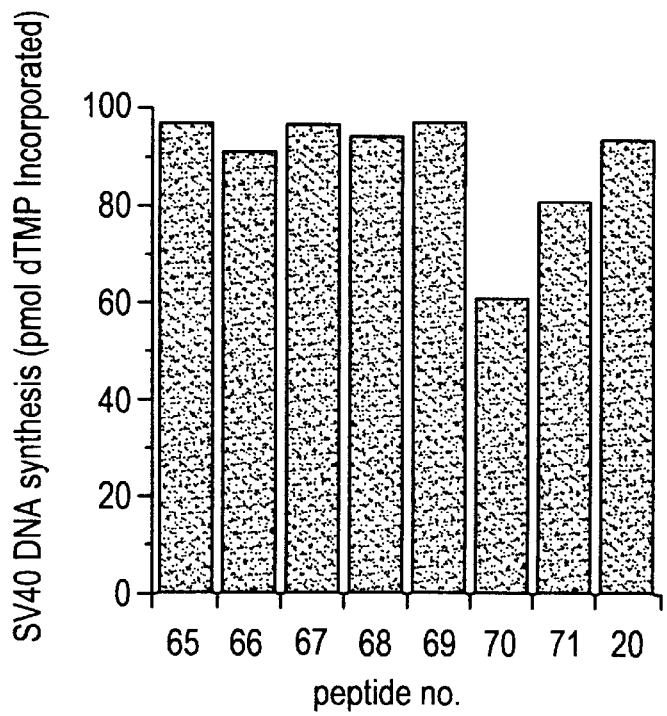

On the basis of the ELISA pepscan information, a new generation of peptides were synthesized to define the critical residues in the PCNA binding site on $p21^{WAF1}$. Firstly, the sequence of peptide 10 was scanned to determine the minimum size of the recognition sequence by creating a set of peptides with 4 amino acid overhangs ie with 16 amino acid overlap between adjacent peptides based on the $p21^{WAF1}$ sequence from amino acids 121 to 164 and including the original reactive peptide of the sequence KRRQTSMTDFYHSKRRLIFS (SEQ ID NO:2) (FIG. 7a). These peptides were immobilised on streptavidin-coated ELISA dishes and screened for binding to PCNA overexpressed in BL21 bacteria. Of the 8 peptides in this array, only peptides designated "68", "69" and "70" bound strongly to PCNA (FIG. 7b). Of these three, peptide "70" (identical to the original peptide 10) showed any appreciable inhibitory activity, although a slight decrease in label incorporation was observed with peptide "71" (FIG. 7c). Interestingly, neither peptide "68" nor "69" showed any capacity to block SV40 replication, despite their ability to bind to PCNA.

Therefore, we conclude that the motif (or a part thereof) of KRRQTSMTDFYH (amino acids 1–12 of SEQ ID NO:2) is required for binding to PCNA, but that the more C-terminal residues SKRRLIFS (SEQ ID NO: 4) may also contribute to PCNA binding.

Figure 8B:
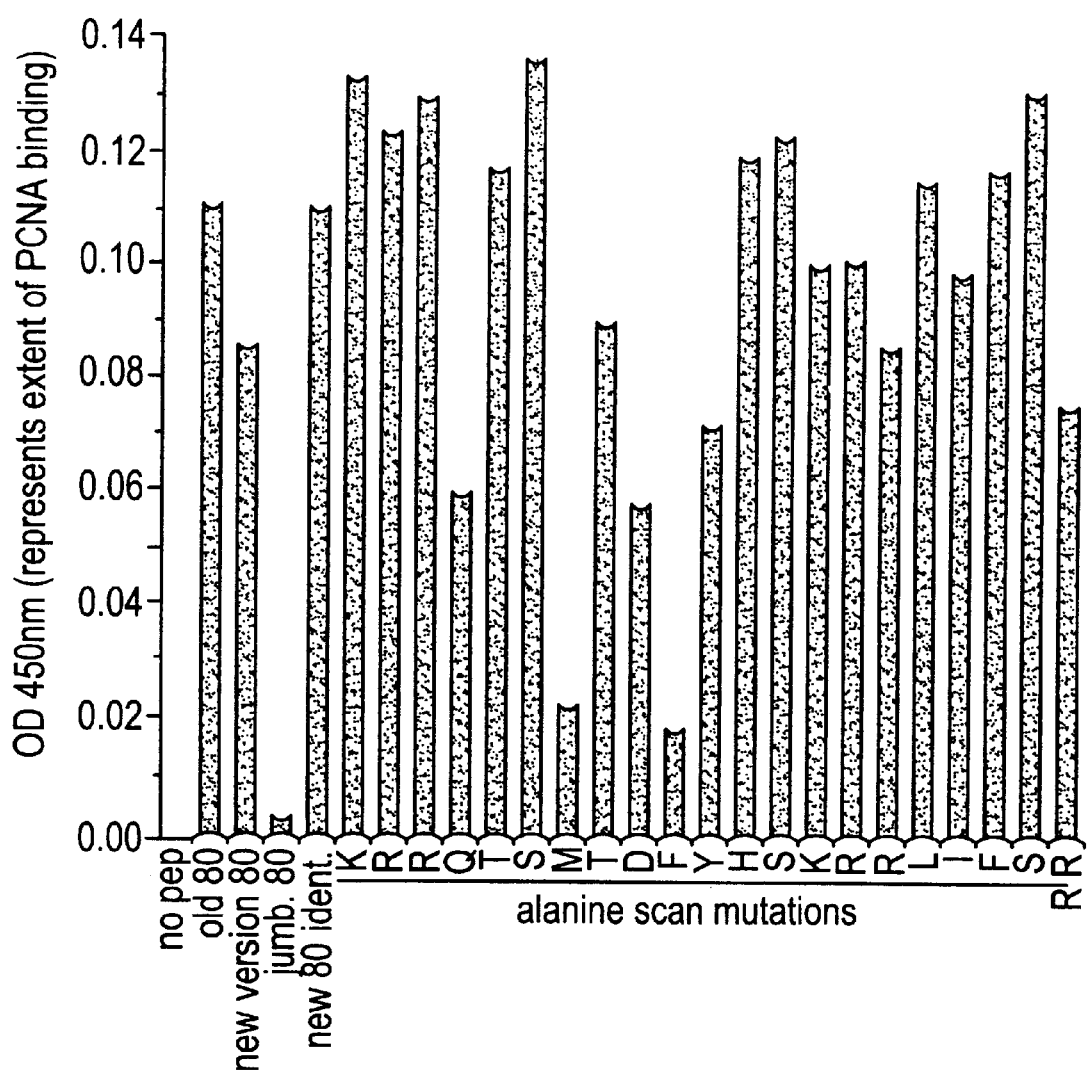
Figure 8C:
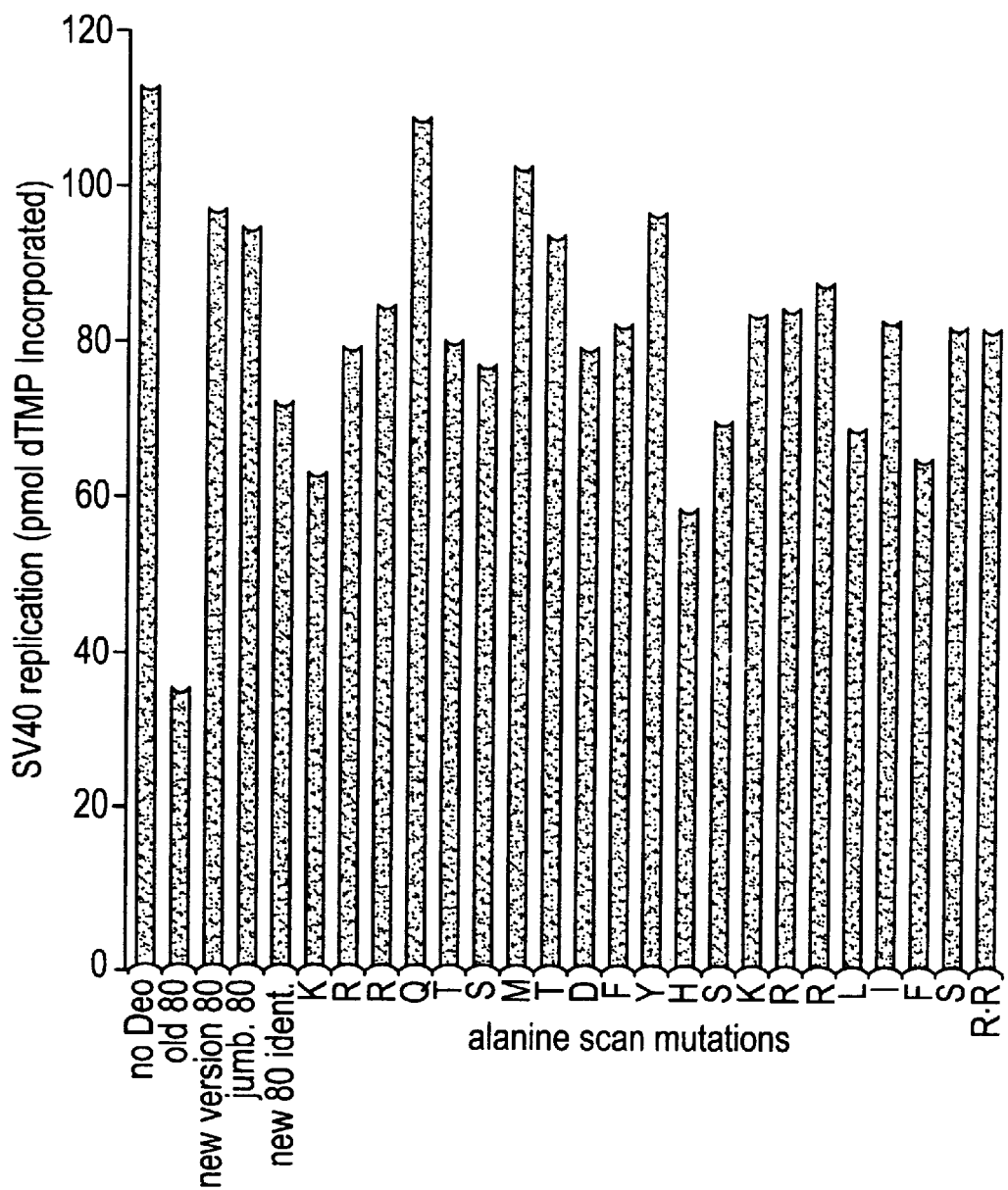

In addition, we generated a series of peptides where each residue of peptide 10 was altered sequentially to alanine, and also a double mutant with two arginines (as marked on FIG. 8a) substituted by alanine. These peptides were tested in ELISA for PCNA binding capacity, and it was found that residues M and F were absolutely required for recognition, while mutation of Q, D or Y considerably decreased the ability to bind PCNA (FIG. 8b). In general, of these altered peptides, those possessing greatest PCNA binding capacity were most able to inhibit the replication of SV40 DNA in vitro, and conversely, loss of PCNA binding correlated with lack of inhibition of SV40 replication (FIG. 8c), although for some peptides (eg a modified form of peptide 10 with an additional 5 amino acids at the N-terminus and a concomitant loss of the C-terminal 5 amino acids), the relationship between PCNA binding and replication inhibition was not as straightforward.

Combining the results of these experiments permits us to define the region of $p21^{WAF1}$ involved in PCNA binding to QTSMTDFY, where residues shown in bold are critical for PCNA binding, and those underlined are important.

In the context of the more N-terminal KRR, a consensus site for phosphorylation of either the serine or threonines eg by cAMP dependent protein kinase is observed, so binding PCNA may be regulated both by primary sequence of $p21^{WAF1}$ as defined here and also by phosphorylation of susceptible sites within this region. In addition, amino acids surrounding the minimal binding site appear to be important for defining the affinity of interaction with PCNA and the biological activity of $p21^{WAF1}$, such as its ability to directly inhibit SV40 DNA replication in vitro.

Thus, the above results demonstrate a strong interaction between PCNA and the C-terminal region of $p21^{WAF1}$ using the yeast two-hybrid screening method. A 20 amino acid peptide from $p21^{WAF1}$ binds PCNA strongly and specifically and is capable of inhibiting DNA replication in vitro. Within the 20 amino acid peptide, an 8 amino acid region was found to define the part of $p21^{WAF1}$ important for PCNA binding.

Thus, these results allow the development of peptides or mimetics that might be used therapeutically to halt DNA replication in tumour and other hyperproliferative cells without compromising the integrity of the genome.

Therapeutic applications of the present invention include the administration of the various peptides mentioned above based on the C-terminal region of $p21^{WAF1}$ in particular the 20 amino acid peptide corresponding to residues 141 to 160, or the 8 amino acid peptide corresponding to residues 144 to 151, or alternatively functional variants or mimetics of these peptides.

Various methods of administration of the therapeutic agent can be used, following known formulations and procedures. Dosages can be determined by routine experimentation. The administration may be systemic or targeted, the latter employing direct (eg topical) application of the therapeutic agent to the target cells or the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, eg in a viral vector (a variant of the VDEPT technique—see below). The vector could be targeted to the specific cells to be treated, or it could contain regulatory elements which are switched on more or less selectively by the target cells.

Alternatively, the agent could be administerd in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, eg an enzyme, in a vector by expression from encoding DNA in a viral vector (see for example, EP-A-415731 and WO 90/07936).

REFERENCES

1. El-Deiry et al., Cell 75 817 (1993).
2. Dulic et al., Cell 76, 1013 (1994).
3. $p21^{WAF1}$ is also known as $p21^{CIP1}$ (9) $p21^{Pic}$ (33) $p20^{CAP}$ (34) and Sdi1 (35).
4. H. Zhang, G. J. Hannon, D. Beach, Genes and Development 8, 1750 (1994).
5. S. Waga, G. J. Hannon, D. Beach, B. Stillman, Nature 369 574 (1994).
6. R. Bravo, R. Frank, P. A. Blundell, H. MacDonald-Bravo, Nature 326, 517 (1987).
7. G. Prelich et al., Nature 326, 517 (1987).
8. Y. Gu, C. W. Turck, D. O. Morgan, Nature 366, 707 (1993).
9. J. W. Harper, G. R. Adami, N. Wei, K Keyomarsi, S. J. Elledge, Cell 75, 805 (1993).
10. Y. Xiong et al., Nature 366, 701 (1993).
11. S. Fields and O. Song, Nature 340, 245 (1989).
12. T. Durfee et al., Genes and Development 7, 555 (1993).
13. The open reading frame of human PCNA cDNA was adapted as NdeI—BamHI fragments using PCR, to give either the full length open reading frame, or the deletion constructs described in FIG. 6. These were subcloned into pBC-SK (Stratagene) and sequenced using oligonucleotide primers on one strand to check for PCR errors. DNA sequencing was performed using double stranded plasmid template DNA with a modification of the Sequenase protocol (USB). Sequence analysis was carried out using the UWGCG package at the Daresbury Seqnet facility. One full length isolate was used to subclone the insert into pAS2 (Harper et al 1993) to give pAS-pcnahs, and also into the vector pREP1 which is used for expression in S.pombe under the control of the nmt1 promoter (Basi 1993). This plasmid pREP1 -pcnahs, was capable of complementing the lethality resulting from pcn1 deletion, suggesting that the protein expressed from this construct is functional. The plasmid pAS-pcnasp was derived from the plasmid pREP1pcn1 (Wasseem et al). The insert in this plasmid was found to contain a frameshift mutation compared to the genomic sequence (data not shown) and was modified before cloning into pAS to ensure that the entire protein was expressed. The plasmid pAS-pcnadm was constructed in a similar fashion to that described above.

14. Tests for reporter gene activation in Y190 were carried out as follows: Y190 transformant colonies were picked to SD plates containing appropriate supplements, and after one or two days growth were tested for LacZ expression using the β-galactosidase filter lift assay (31). The HIS3 reporter construct described here gives residual His3 expression, though not sufficient to render the cells resistant to 3 -aminotriazole, which is a chemical inhibitor of His3 (IPG dehydratase) at 50 mM. Cells were streaked out on SD plates containing 50 mM 3 -aminotriazole, incubated for 1 week, and plates examined for the formation of single colonies. Where growth occurred, a filter lift was taken from these plates to assay β-galactosidase activity. Only transformants which expressed both reporter genes were counted as true positives.

15. K. Polyak et al., Cell 78, 59 (1994)
16. H. Toyoshima and T. Hunter, Cell 78, 67 (1994)
17. N. H. Wasseem, K. Labib, P. Nurse, D. P. Lane, EMBO J. 11, 5111 (1992).
18. X-P. Kong, R Onrust, M. O'Donnell, J. Kuriyan, Cell 69, 425 (1992).
19. Peptides were synthesized by Chiron Mimotopes, Australia, representing the entire $p21^{WAF1}$ protein as 20 amino acid stretches, linked to biotin by a four amino acid linker of SGSG. Peptides were dissolved in DMSO to 5 mg/ml and stored at −80° C.
20. S. M. Picksley, B. Vojtesek, A.Sparks, D.P.Lane, Oncogene 9, 2523 (1994).
21. G. Roos et al., Lab. Invest. 68, 204 (1993).
22. M. E. A. Churchill et al., J. Mol. Biol. 241, 534 (1994).
23. T. Melendey and B. Stillman, J. Biol. Chem. 266, 1942 (1991).
24. Plastic ELISA plates (Falcon) were coated overnight at 37° C. with 5 µg/ml streptavidin (Vector), washed with PBS with 0.20. Tween 20 (PBST) then blocked in 5% non-fat milk powder in PBS for 2 h at room temperature (r.t.). Each well of the plates was incubated with the following, washing extensively between each incubation with PBST: (i) 0.5 µg peptide diluted in 0.1% milk-PBS, 1h r.t., (ii) 6 µg total protein from cell extracts, 1 h r.t. diluted in 0.1% milk-PBS, (iii) primary antibody 3009 at 1:1000 in 2% milk-PBST or undiluted hybridoma supernatant of PC10 , 1 h r.t., (iv) secondary horse-radish peroxidase conjugated anti-rabbit (for 3009) or anti-mouse antibody (for PC10) at 1:1000 in 2% milk-PBST, 1 h r.t., then 50 µl of the chromogenic substrate TMB was added per well (prepared from 10 mg/ml stock in DMSO and diluted to 100 μg/ml final concentration in 0.1 M sodium acetate pH 6.0 with 1:1000 30% stock solution H202). Once a visible blue colour had developed, the reaction was stopped by addition of 1M $H_2SO_4$, and the plate read using a Dynatech 5000 ELISA plate reader at 450 nm.

25. L. S. Cox, S. Picksley, P. A. Hall, A. T. M. Rennie, D. P. Lane, unpublished material.

26. N. Wasseem and D. P. Lane, J. Cell Sci. 96, 121 (1990)

27. Human PCNA was purified from lysates of BL21 transformed with pT7.7hPCNA construct (23).

28. 1.5 μg of peptide was bound to 10μl packed streptavidin-agarose beads for 1 hour at room temperature. The beads were washed extensively in PBS prior to incubation with 20 μg total cell protein for 1 hour at 4° C. After washing three times in 1.5×PBS (220 mM NaCl), the beads were boiled in SDS with DTT then proteins were separated by 10% SDS-PAGE and either stained directly with Coomassie brilliant blue or electrophoretically transferred to nitrocellulose. Blots were blocked in 5% non-fat milk powder in PBS with 0.2% Tween 20 (PBST), washed in PBS and incubated with undiluted culture supernatant from PC10 hybridomas, followed by horse-radish peroxidase conjugated rabbit anti-mouse antibody (Dako) at 1:1000 dilution in 2% milk-PBST. Proteins were visualised by the ECL reaction using Hyperfilm-MP (Amersham, UK).

29. SV40 replication reactions were carried out essentially as described by Wang et al 1991, with the exception that all incubation volumes were 10 μl.

30. Growth and maintenance of S.cerevisiae was according to Rose et al., (39). Transformation was carried out by the method of Gietz et al., (40). All growth was carried out at 30° C. The S.cerevisiae strain Y190 (MATa leu2-3, 112, ura3-52, trp1-901, his3-D200, ade2-101, gal4D, gal80D, $cyh^R$ URA3::GAL1-lacZ, LYS2::GAL1-HIS3) was used for all two-hybrid analysis.

31. L. Breeden, K. Nasmyth, Cold Spring Harbor Symp. Quant. Biol. 50, 643 (1985).

32. Plasmid DNA was recovered from S. cerevisiae using a modified version of the method described by Hoffman and Winston (38) and further purified using GeneClean™ (Stratagene). The E.coli strain JA226 (recBC leuB6 trpES hsdR−hsdM+lacY600) was used to recover expression plasmids from S. cerevisiae. $Amp^R$ colonies were tested for leucine prototrophy to determine whether they contained a pACT or pAS2 derived plasmid; the LEU2 sequences in pACT complement the leuB6 mutation in JA226.

33. T. Hunter, Cell 75, 839 (1993)

34. Y. Gu, C. W. Turck, D. O. Morgan, Nature 366, 707 (1993).

35. A. Noda, Y. Ning, S. F. Venable, O. M. Pereira Smith, J. R. Smith, Exp. Cell. Res. 211, 90 (1994).

36. E. H. Wang, P. N. Friedman, C. Prives, Cell 57, 379 (1991).

37. G. Basi, E. Schmid, K. Moundrell, Gene 123, 131 (1993).

38. C. S. Hoffman, F. Winston, Gene 57, 267 (1987).

39. M. D. Rose, F. Winston, and P Hieter Methods in Yeast Genetics; a Laboratory Manual (Cold Spring Harbor Laboratory Press, Cold Spring Harbor, N. Y.,1990).

40. D. Gietz, A. St John, R. A. Woods, R. H. Schiestl, Nucleic Acid Res. 20, 1425 (1992).

What is claimed is:

1. A substance which has the property of binding to proliferating cell nuclear antigen (PCNA), wherein the substance is selected from the group consisting of:
   (i) a fragment of the p21$^{WAF1}$ protein comprising residues 141 to 160 of the p21$^{WAF1}$ amino acid sequence, or derivative thereof comprising the amino acid motif MXXF;
   (ii) a non-peptide functional mimetic of said fragment or said derivative thereof; and
   (iii) a peptide consisting of the amino acid sequence KRRQTSMTDFYH (amino acids 1–12 of SEQ ID NO:2) or a fragment or derivative thereof comprising the amino acid motif MXXF.

2. The substance of claim 1, wherein said substance is a fragment or derivative of the p21$^{WAF1}$ protein comprising the amino acid motif QXXMXDFY (SEQ ID NO:41).

3. The substance of claim 1 wherein the substance is a peptide of the p21$^{WAF}$ protein comprising residues 144 to 151 of the p21$^{WAF1}$ amino acid sequence.

4. The substance of any one of claims 1–3 wherein the binding of the substance to PCNA inhibits DNA replication.

5. A composition comprising the substance of any one of claims 1 to 3, in combination with a carrier.

6. A method of screening for polypeptides or peptidyl mimetics which bind to PCNA comprising:
  (i) transforming yeast cells with a vector expressing a fusion of a DNA binding domain of Gal4 and PCNA, the yeast cells comprising one or more reporter constructs under the control of a Gal1 promoter;
  (ii) transforming said yeast cells with a vector expressing a fusion of an activation domain of Gal4 and a candidate polypeptide or peptidyl mimetic;
  (iii) detecting the transcription of the reporter constructs caused when a candidate polypeptide or peptidyl mimetic binds to PCNA and results in Gal4 transcriptional activity.

7. The method according to claim 6 wherein the candidate peptide or peptidyl mimetic is a polypeptide or peptidyl mimetic of p21$^{WAF1}$ protein.

8. A peptide which has the property of binding to proliferating cell nuclear antigen (PCNA), wherein said peptide consists of 8 amino acid residues and comprises the motif MXXF.

9. The peptide of claim 8, said peptide having the motif QXXMXDFY (SEQ ID NO:41).

10. A method of inhibiting DNA replication comprising contacting a cell with a substance which has the property of binding to proliferating cell nuclear antigen (PCNA), wherein the substance is:
  (i) a fragment of the p21$^{WAF1}$ protein comprising residues 141 to 160 of the p21$^{WAF1}$ amino acid sequence, or an active portion or derivative thereof comprising the amino acid motif MXXF; or,
  (ii) a functional mimetic of said protein fragment.

11. The method of claim 10, wherein said fragment comprises the amino acid motif QXXMXDFY (SEQ ID NO:41).

12. A method of inhibiting DNA replication comprising contacting a cell with a substance which has the property of binding to proliferating cell nuclear antigen (PCNA), said substance comprising a peptide based on the C-terminal region of p21$^{WAF1}$, wherein said peptide comprises the amino acid sequence QXXMXDFY (SEQ ID NO:41), or a functional mimetic of said peptide.

13. A peptide fragment of the p21$^{WAF1}$ protein which has the property of binding to proliferating cell nuclear antigen (PCNA), wherein the peptide fragment is selected from the group consisting of:
  (i) a peptide fragment comprising residues 141 to 160 of the p21$^{WAF1}$ amino acid sequence,
  (ii) a peptide fragment consisting of the amino acid sequence KRRQTSMTDFYH (amino acids 1–12 of SEQ ID NO:2) and,
  (iii) an 8 amino acid peptide comprising the amino acid motif QXXMXDFY (SEQ ID NO:41).

14. A derivative of the peptide fragment of claim 13, wherein said derivative comprises the motif QXXMXDFY (SEQ ID NO:41).

15. A non-peptide mimetic based on the peptide fragment of claim 13.

16. A method of inhibiting DNA replication comprising contacting a cell with a peptide which has the property of binding to proliferating cell nuclear antigen (PCNA), said peptide comprising the amino acid motif QXXMXDFY (SEQ ID NO:41).

* * * * *

SEQUENCE LISTING

```
<160> NUMBER OF SEQ ID NOS: 41

<210> SEQ ID NO 1
<211> LENGTH: 8
<212> TYPE: PRT
<213> ORGANISM: Homo sapiens

<400> SEQUENCE: 1

Gln Thr Ser Met Thr Asp Phe Tyr
 1               5

<210> SEQ ID NO 2
<211> LENGTH: 20
<212> TYPE: PRT
<213> ORGANISM: Homo sapiens

<400> SEQUENCE: 2

Lys Arg Arg Gln Thr Ser Met Thr Asp Phe Tyr His Ser Lys Arg Arg
 1               5                  10                  15

Leu Ile Phe Ser
            20

<210> SEQ ID NO 3
<211> LENGTH: 8
<212> TYPE: PRT
<213> ORGANISM: Homo sapiens
```

-continued

```
<400> SEQUENCE: 3

Gln Thr Ser Met Thr Asp Phe Tyr
  1               5

<210> SEQ ID NO 4
<211> LENGTH: 8
<212> TYPE: PRT
<213> ORGANISM: Homo sapiens

<400> SEQUENCE: 4

Ser Lys Arg Arg Leu Ile Phe Ser
  1               5

<210> SEQ ID NO 5
<211> LENGTH: 20
<212> TYPE: PRT
<213> ORGANISM: Homo sapiens

<400> SEQUENCE: 5

Met Ser Glu Pro Ala Gly Asp Val Arg Gln Asn Pro Cys Gly Ser Lys
  1               5                  10                  15

Ala Cys Arg Arg
            20

<210> SEQ ID NO 6
<211> LENGTH: 20
<212> TYPE: PRT
<213> ORGANISM: Homo sapiens

<400> SEQUENCE: 6

Lys Ala Cys Arg Arg Leu Phe Gly Pro Val Asp Ser Glu Gln Leu Ser
  1               5                  10                  15

Arg Asp Cys Asp
            20

<210> SEQ ID NO 7
<211> LENGTH: 20
<212> TYPE: PRT
<213> ORGANISM: Homo sapiens

<400> SEQUENCE: 7

Ser Arg Asp Cys Asp Ala Leu Met Ala Gly Cys Ile Gln Glu Ala Arg
  1               5                  10                  15

Glu Arg Trp Asn
            20

<210> SEQ ID NO 8
<211> LENGTH: 20
<212> TYPE: PRT
<213> ORGANISM: Homo sapiens

<400> SEQUENCE: 8

Arg Glu Arg Trp Asn Phe Asp Phe Val Thr Glu Thr Pro Leu Glu Gly
  1               5                  10                  15

Asp Phe Ala Trp
            20

<210> SEQ ID NO 9
<211> LENGTH: 20
<212> TYPE: PRT
<213> ORGANISM: Homo sapiens
```

-continued

```
<400> SEQUENCE: 9

Gly Asp Phe Ala Trp Glu Arg Val Arg Gly Leu Gly Leu Pro Lys Leu
 1               5                  10                  15

Tyr Leu Pro Thr
            20

<210> SEQ ID NO 10
<211> LENGTH: 20
<212> TYPE: PRT
<213> ORGANISM: Homo sapiens

<400> SEQUENCE: 10

Leu Tyr Leu Pro Thr Gly Pro Arg Arg Gly Arg Asp Glu Leu Gly Gly
 1               5                  10                  15

Gly Arg Arg Pro
            20

<210> SEQ ID NO 11
<211> LENGTH: 20
<212> TYPE: PRT
<213> ORGANISM: Homo sapiens

<400> SEQUENCE: 11

Gly Gly Arg Arg Pro Gly Thr Ser Pro Ala Leu Leu Gln Gly Thr Ala
 1               5                  10                  15

Glu Glu Asp His
            20

<210> SEQ ID NO 12
<211> LENGTH: 20
<212> TYPE: PRT
<213> ORGANISM: Homo sapiens

<400> SEQUENCE: 12

Ala Glu Glu Asp His Val Asp Leu Ser Leu Ser Cys Thr Leu Val Pro
 1               5                  10                  15

Arg Ser Gly Glu
            20

<210> SEQ ID NO 13
<211> LENGTH: 20
<212> TYPE: PRT
<213> ORGANISM: Homo sapiens

<400> SEQUENCE: 13

Pro Arg Ser Gly Glu Gln Ala Glu Gly Ser Pro Gly Gly Pro Gly Asp
 1               5                  10                  15

Ser Gln Gly Arg
            20

<210> SEQ ID NO 14
<211> LENGTH: 20
<212> TYPE: PRT
<213> ORGANISM: Homo sapiens

<400> SEQUENCE: 14

Thr Ser Met Thr Asp Phe Tyr His Ser Lys Arg Arg Leu Ile Phe Ser
 1               5                  10                  15

Lys Arg Lys Pro
            20
```

```
<210> SEQ ID NO 15
<211> LENGTH: 15
<212> TYPE: PRT
<213> ORGANISM: Homo sapiens

<400> SEQUENCE: 15

Leu Lys Tyr Tyr Leu Ala Pro Lys Ile Glu Asp Glu Glu Gly Ser
 1               5                  10                  15

<210> SEQ ID NO 16
<211> LENGTH: 20
<212> TYPE: PRT
<213> ORGANISM: Homo sapiens

<400> SEQUENCE: 16

Glu Gln Ala Glu Gly Ser Pro Gly Gly Pro Gly Asp Ser Gln Gly Arg
 1               5                  10                  15

Lys Arg Arg Gln
            20

<210> SEQ ID NO 17
<211> LENGTH: 20
<212> TYPE: PRT
<213> ORGANISM: Homo sapiens

<400> SEQUENCE: 17

Gly Ser Pro Gly Gly Pro Gly Asp Ser Gln Gly Arg Lys Arg Arg Gln
 1               5                  10                  15

Thr Ser Met Thr
            20

<210> SEQ ID NO 18
<211> LENGTH: 20
<212> TYPE: PRT
<213> ORGANISM: Homo sapiens

<400> SEQUENCE: 18

Gly Pro Gly Asp Ser Gln Gly Arg Lys Arg Arg Gln Thr Ser Met Thr
 1               5                  10                  15

Asp Phe Tyr His
            20

<210> SEQ ID NO 19
<211> LENGTH: 20
<212> TYPE: PRT
<213> ORGANISM: Homo sapiens

<400> SEQUENCE: 19

Ser Gln Gly Arg Lys Arg Arg Gln Thr Ser Met Thr Asp Phe Tyr His
 1               5                  10                  15

Ser Lys Arg Arg
            20

<210> SEQ ID NO 20
<211> LENGTH: 19
<212> TYPE: PRT
<213> ORGANISM: Homo sapiens

<400> SEQUENCE: 20

Asp Phe Tyr His Ser Lys Arg Arg Leu Ile Phe Ser Lys Arg Lys Pro
 1               5                  10                  15

Gly Asp Ser
```

<210> SEQ ID NO 21
<211> LENGTH: 20
<212> TYPE: PRT
<213> ORGANISM: Homo sapiens

<400> SEQUENCE: 21

Ala Arg Arg Gln Thr Ser Met Thr Asp Phe Tyr His Ser Lys Arg Arg
 1               5                  10                  15

Leu Ile Phe Ser
            20

<210> SEQ ID NO 22
<211> LENGTH: 20
<212> TYPE: PRT
<213> ORGANISM: Homo sapiens

<400> SEQUENCE: 22

Lys Ala Arg Gln Thr Ser Met Thr Asp Phe Tyr His Ser Lys Arg Arg
 1               5                  10                  15

Leu Ile Phe Ser
            20

<210> SEQ ID NO 23
<211> LENGTH: 20
<212> TYPE: PRT
<213> ORGANISM: Homo sapiens

<400> SEQUENCE: 23

Lys Arg Ala Gln Thr Ser Met Thr Asp Phe Tyr His Ser Lys Arg Arg
 1               5                  10                  15

Leu Ile Phe Ser
            20

<210> SEQ ID NO 24
<211> LENGTH: 20
<212> TYPE: PRT
<213> ORGANISM: Homo sapiens

<400> SEQUENCE: 24

Lys Arg Arg Ala Thr Ser Met Thr Asp Phe Tyr His Ser Lys Arg Arg
 1               5                  10                  15

Leu Ile Phe Ser
            20

<210> SEQ ID NO 25
<211> LENGTH: 20
<212> TYPE: PRT
<213> ORGANISM: Homo sapiens

<400> SEQUENCE: 25

Lys Arg Arg Gln Ala Ser Met Thr Asp Phe Tyr His Ser Lys Arg Arg
 1               5                  10                  15

Leu Ile Phe Ser
            20

<210> SEQ ID NO 26
<211> LENGTH: 20
<212> TYPE: PRT
<213> ORGANISM: Homo sapiens

```
<400> SEQUENCE: 26

Lys Arg Arg Gln Thr Ala Met Thr Asp Phe Tyr His Ser Lys Arg Arg
 1               5                  10                  15

Leu Ile Phe Ser
         20

<210> SEQ ID NO 27
<211> LENGTH: 20
<212> TYPE: PRT
<213> ORGANISM: Homo sapiens

<400> SEQUENCE: 27

Lys Arg Arg Gln Thr Ser Ala Thr Asp Phe Tyr His Ser Lys Arg Arg
 1               5                  10                  15

Leu Ile Phe Ser
         20

<210> SEQ ID NO 28
<211> LENGTH: 20
<212> TYPE: PRT
<213> ORGANISM: Homo sapiens

<400> SEQUENCE: 28

Lys Arg Arg Gln Thr Ser Met Ala Asp Phe Tyr His Ser Lys Arg Arg
 1               5                  10                  15

Leu Ile Phe Ser
         20

<210> SEQ ID NO 29
<211> LENGTH: 20
<212> TYPE: PRT
<213> ORGANISM: Homo sapiens

<400> SEQUENCE: 29

Lys Arg Arg Gln Thr Ser Met Thr Ala Phe Tyr His Ser Lys Arg Arg
 1               5                  10                  15

Leu Ile Phe Ser
         20

<210> SEQ ID NO 30
<211> LENGTH: 20
<212> TYPE: PRT
<213> ORGANISM: Homo sapiens

<400> SEQUENCE: 30

Lys Arg Arg Gln Thr Ser Met Thr Asp Ala Tyr His Ser Lys Arg Arg
 1               5                  10                  15

Leu Ile Phe Ser
         20

<210> SEQ ID NO 31
<211> LENGTH: 20
<212> TYPE: PRT
<213> ORGANISM: Homo sapiens

<400> SEQUENCE: 31

Lys Arg Arg Gln Thr Ser Met Thr Asp Phe Ala His Ser Lys Arg Arg
 1               5                  10                  15

Leu Ile Phe Ser
         20
```

<210> SEQ ID NO 32
<211> LENGTH: 20
<212> TYPE: PRT
<213> ORGANISM: Homo sapiens

<400> SEQUENCE: 32

Lys Arg Arg Gln Thr Ser Met Thr Asp Phe Tyr Ala Ser Lys Arg Arg
 1               5                  10                  15

Leu Ile Phe Ser
            20

<210> SEQ ID NO 33
<211> LENGTH: 20
<212> TYPE: PRT
<213> ORGANISM: Homo sapiens

<400> SEQUENCE: 33

Lys Arg Arg Gln Thr Ser Met Thr Asp Phe Tyr His Ala Lys Arg Arg
 1               5                  10                  15

Leu Ile Phe Ser
            20

<210> SEQ ID NO 34
<211> LENGTH: 20
<212> TYPE: PRT
<213> ORGANISM: Homo sapiens

<400> SEQUENCE: 34

Lys Arg Arg Gln Thr Ser Met Thr Asp Phe Tyr His Ser Ala Arg Arg
 1               5                  10                  15

Leu Ile Phe Ser
            20

<210> SEQ ID NO 35
<211> LENGTH: 20
<212> TYPE: PRT
<213> ORGANISM: Homo sapiens

<400> SEQUENCE: 35

Lys Arg Arg Gln Thr Ser Met Thr Asp Phe Tyr His Ser Lys Ala Arg
 1               5                  10                  15

Leu Ile Phe Ser
            20

<210> SEQ ID NO 36
<211> LENGTH: 20
<212> TYPE: PRT
<213> ORGANISM: Homo sapiens

<400> SEQUENCE: 36

Lys Arg Arg Gln Thr Ser Met Thr Asp Phe Tyr His Ser Lys Arg Ala
 1               5                  10                  15

Leu Ile Phe Ser
            20

<210> SEQ ID NO 37
<211> LENGTH: 20
<212> TYPE: PRT
<213> ORGANISM: Homo sapiens

```
<400> SEQUENCE: 37

Lys Arg Arg Gln Thr Ser Met Thr Asp Phe Tyr His Ser Lys Arg Arg
  1               5                  10                  15

Ala Ile Phe Ser
            20

<210> SEQ ID NO 38
<211> LENGTH: 20
<212> TYPE: PRT
<213> ORGANISM: Homo sapiens

<400> SEQUENCE: 38

Lys Arg Arg Gln Thr Ser Met Thr Asp Phe Tyr His Ser Lys Arg Arg
  1               5                  10                  15

Leu Ala Phe Ser
            20

<210> SEQ ID NO 39
<211> LENGTH: 20
<212> TYPE: PRT
<213> ORGANISM: Homo sapiens

<400> SEQUENCE: 39

Lys Arg Arg Gln Thr Ser Met Thr Asp Phe Tyr His Ser Lys Arg Arg
  1               5                  10                  15

Leu Ile Ala Ser
            20

<210> SEQ ID NO 40
<211> LENGTH: 20
<212> TYPE: PRT
<213> ORGANISM: Homo sapiens

<400> SEQUENCE: 40

Lys Ala Arg Gln Thr Ser Met Thr Asp Phe Tyr His Ser Lys Ala Arg
  1               5                  10                  15

Leu Ile Phe Ser
            20

<210> SEQ ID NO 41
<211> LENGTH: 8
<212> TYPE: PRT
<213> ORGANISM: Homo sapiens
<220> FEATURE:
<223> OTHER INFORMATION: X's at positions 2,3,5 can be any amino acid

<400> SEQUENCE: 41

Gln Xaa Xaa Met Xaa Asp Phe Tyr
  1               5
```